United States Patent
Keys et al.

(10) Patent No.: US 6,593,091 B2
(45) Date of Patent: Jul. 15, 2003

(54) OLIGONUCLEOTIDE PROBES FOR DETECTING NUCLEIC ACIDS THROUGH CHANGES IN FLOURESCENCE RESONANCE ENERGY TRANSFER

(75) Inventors: Daniel A. Keys, Irvine, CA (US); Firdous Farooqui, Brea, CA (US); M. Parameswara Reddy, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/962,040

(22) Filed: Sep. 24, 2001

(65) Prior Publication Data

US 2003/0096242 A1 May 22, 2003

(51) Int. Cl.⁷ .............................. C12Q 1/68; C12P 19/34
(52) U.S. Cl. .......................................... 435/6; 435/91.2
(58) Field of Search ............................ 435/6, 91.2, 810

(56) References Cited

U.S. PATENT DOCUMENTS

| | | | |
|---|---|---|---|
| 4,725,537 A | 2/1988 | Fritsch et al. | 435/6 |
| 4,996,143 A | 2/1991 | Heller et al. | 435/6 |
| 5,210,015 A | 5/1993 | Gelfand et al. | 435/6 |
| 5,413,908 A | 5/1995 | Jeffreys | 435/6 |
| 5,484,904 A | 1/1996 | Nilsen et al. | 536/23.1 |
| 5,532,129 A | 7/1996 | Heller | 435/6 |
| 5,538,848 A | 7/1996 | Livak et al. | 435/5 |
| 5,565,322 A | * 10/1996 | Heller | 435/6 |
| 5,607,834 A | 3/1997 | Bagwell | 435/6 |
| 5,691,145 A | 11/1997 | Pitner et al. | 435/6 |
| 5,716,784 A | 2/1998 | Di Cesare | 435/6 |
| 5,723,591 A | 3/1998 | Livak et al. | 536/22.1 |
| 5,846,719 A | 12/1998 | Brenner et al. | 435/6 |
| 5,888,739 A | 3/1999 | Pitner et al. | 435/6 |
| 5,925,517 A | 7/1999 | Tyagi et al. | 435/6 |
| 5,928,862 A | 7/1999 | Morrison | 435/6 |
| 5,935,791 A | 8/1999 | Nadeau et al. | 435/6 |
| 5,952,180 A | 9/1999 | Ju | 435/6 |
| 6,013,445 A | 1/2000 | Albrecht et al. | 435/6 |
| 6,054,266 A | 4/2000 | Kronick et al. | 435/6 |
| 6,140,054 A | 10/2000 | Wittwer et al. | 435/6 |
| 6,172,214 B1 | 1/2001 | Brenner | 536/24.3 |

OTHER PUBLICATIONS

Morrison, Larry et al., *Sensitive Fluorescence–Based Thermodynamic and Kinetic Measurements of DNA Hybridization in Solution,* Biochemistry (1993), vol. 32, pp. 3095–3104.

Morrison, Larry et al., *Solution–Phase Detection of Polynucleotides Using Interacting Fluorescent Labels and Competitive Hubridization,* Analytical Biochemistry (1989), vol. 183, pp. 231–244.

Morrison, Larry et al., *Homogenous Detection of Specific DNA Sequences by Fluorescence Quenching and Energy Transfer,* Journal of Fluorescence (1999), vol. 9, pp. 187–196.

* cited by examiner

*Primary Examiner*—Kenneth R. Horlick
(74) *Attorney, Agent, or Firm*—Sheldon & Mak; William H. May; D. David Hill

(57) ABSTRACT

Oligonucleotide probes, kits, and methods useful for detecting a polynucleotide target in a sample are provided. The method, a mixture is formed by combining a polynucleotide target sample, a first probe that is complementary to the polynucleotide target and having a first fluorescent donor or fluorescent acceptor; and a second probe that is partially complementary to the first probe and having a second fluorescent donor or fluorescent acceptor. The second probe competes with the polynucleotide target for binding to the first probe and the first probe preferentially binds to the polynucleotide target rather than to the second probe. The first fluorescent donor or acceptor and second fluorescent donor or acceptor form a donor/acceptor pair capable of fluorescence resonance energy transfer (FRET) with each other in response to activation of the fluorescent donor by light of a predetermined wavelength or band of wavelengths.

29 Claims, 4 Drawing Sheets

A

Probe pair in absence of polynucleotide target

B

Probe pair in presence of polynucleotide target

Probe pair in absence of polynucleotide target

Probe pair in presence of polynucleotide target

A

B

| Absence of Polynucleotide Target (Energy Transfer) | Presence of Polynucleotide Target (Loss of Energy Transfer) |

OLIGONUCLEOTIDE PROBES FOR DETECTING NUCLEIC ACIDS THROUGH CHANGES IN FLOURESCENCE RESONANCE ENERGY TRANSFER

BACKGROUND

The following description provides a summary of information relevant to the present invention and is not a concession that any of the information provided or publications referenced herein is prior art to the presently claimed invention.

There are several types of assays that utilize polynucleotide hybridization probes having fluorescent donor and fluorescent acceptors that generate a fluorescence-based signal in response to a change in the distance and interaction with each other. Such probes have been used to monitor hybridization assays and nucleic acid or polynucleotide amplification reactions by monitoring the appearance, disappearance, or change in intensity of the fluorescence signal generated by the reporter molecule.

These assays typically utilize fluorescence resonance energy transfer (FRET) for signal generation, in which fluorescence is altered by a change in the distance separating a fluorescence resonance energy donor moiety from a fluorescence resonance energy acceptor moiety that is either another fluorophore or a quencher. These combinations of a fluorophore and an interacting molecule or moiety are known as "FRET pairs". A transfer of energy between two members of a FRET-pair requires that the absorption spectrum of the second member of the pair overlaps the emission spectrum of the first member of the pair.

Oligonucleotide probes have been developed where the intensity of fluorescence of a reporter molecule or a FRET-pair increases due to the separation of a reporter molecule from a quencher molecule. Alternatively, there are probes that lose their fluorescence as a result of a quencher molecule being brought into close proximity with a reporter molecule.

One polynucleotide hybridization assay utilizes a pair of oligodeoxynucleotide probes that are completely complementary to each other and to complementary strands of a target DNA (see Morrison, L. E., Halder, T. C. and Stols, L. M., "Solution phase detection of polynucleotides using interacting fluorescent labels and competitive hybridization", *Analyt. Biochem.* 183, 231–244 (1989); Morrison, L. E. and Stols, L. M., "Sensitive fluorescence-based thermodynamic and kinetic measurements of DNA hybridization in solution", *Biochemistry* 32, 3095–3104 (1993), U.S. Pat. No. 5,928,862 to Morrison). Each probe includes a fluorophore dye conjugated to its 3' end and a quenching moiety conjugated to its 5' end. The probes are long enough to prevent self-quenching when they are hybridized to the target. Upon hybridization of the two oligonucleotide probes, the fluorophore of each probe is positioned in close proximity to the quenching moiety of the other probe. This results in a quenching of the fluorescent label by the quenching moiety when the fluorescent label is stimulated by an appropriate frequency of light. The quenching effect of the complementary probe is removed when either probe is bound to a target. A problem with this assay is that there are two opposing design parameters required for optimization of the assay. As an initial consideration, it is beneficial to have a high concentration of probes to assure that hybridization of probes to target is rapid. However, a high concentration of probes results in an increase in background fluorescence that results from unhybridized probes. Since it is generally more important to minimize background fluorescence, a less than optimal concentration of probes is typically used. Accordingly, the kinetics of the reaction are unfavorable and the assay is slow. Typically, it is necessary to delay reading the residual fluorescence to permit nearly all the excess probes to anneal to their complements. Real-time detection is not practical with this assay. Another polynucleotide hybridization assay that utilizes a FRET pair is the "TaqMan" method described in Gelfand et al. U.S. Pat. No. 5,210,015, and Livak et al. U.S. Pat. No. 5,538,848. In this assay the probe is a single-stranded oligonucleotide labeled with a reporter and quencher molecule of a FRET pair at either end of the probe. A nucleic acid polymerase having 5' to 3' exonuclease activity releases single or multiple nucleotides by cleavage of the oligonucleotide probe when it is hybridized to a target strand. These cleavages separate the quencher label and the fluorophore label of the FRET pair. The assay requires treatment with the described polymerase, and further requires that the sample nucleic acid be amplified by the polymerase chain reaction (PCR). The synthesis of oligonucleotides carrying two different labels in specific locations is complex and requires labor-intensive purification, resulting in higher cost. Another type of polynucleotide hybridization probe assay utilizing FRET pairs is described in U.S. Pat. No. 5,925,517 to Tyagi et al. This assay utilizes labeled oligonucleotide probes referred to as "Molecular Beacons" which have a central region and two end regions. The end regions hybridize with one another in the absence of target, but the end regions are separated when the central portion of the probe hybridizes to a complementary target sequence. The probes utilized in this assay are large, relatively complicated in design, and more expensive. Each of the above described methods suffers from one or more disadvantages. Accordingly, there is a need for a polynucleotide detection method and probes that is more sensitive than alternatives, more flexible, cheaper, simpler, and faster than alternatives.

SUMMARY

The invention satisfies this need. The present invention provides oligonucleotide probes and methods of using the probes for detecting one or more polynucleotide targets in a sample. In one embodiment the method is performed by first forming a mixture by combining (a) a sample known to contain or suspected of containing the polynucleotide target; (b) a first probe complementary to the polynucleotide target and comprising a first fluorescence donor or acceptor; and (c) a second probe partially complementary to the first probe and comprising a second fluorescence donor or acceptor. The second probe competes with the polynucleotide target for binding to the first probe, and the first probe preferentially binds to the polynucleotide target rather than to the second probe. The first fluorescence donor or acceptor and the second fluorescence donor or acceptor are a fluorescent donor/acceptor pair capable of fluorescence resonance energy transfer with each other in response to activation of the fluorescence donor by light of a predetermined wavelength or band of wavelengths. Upon hybridization of the first probe to the second probe, the fluorescent donor and fluorescent acceptor are spaced apart from each other a distance such that they are capable of fluorescence resonance energy transfer in response to activation of the fluorescent donor by light of the predetermined wavelength or band of wavelengths. The second step of the method is activating the fluorescent donor in the mixture with light of the predetermined wavelength or band of wavelengths. The last step is detecting light emitted by the fluorescent donor, the fluorescent acceptor, or both fluorescent donor and fluorescent acceptor.

The invention further includes methods for detecting more than one polynucleotide target in a sample. The method is performed by forming a mixture by combining more than one probe pair and one or more samples known to contain or suspected of containing more than one polynucleotide target. Each probe pair comprises a first probe and a second probe. Each probe of a probe pair comprises a fluorescent donor or acceptor such that each probe pair forms a fluorescent donor/acceptor pair capable of fluorescence resonance energy transfer in response to activation of the fluorescent donor by light of a predetermined wavelength or band of wavelengths. For each probe pair, the first probe is complementary to the polynucleotide target and the second probe of a probe pair is partially complementary to the first probe. The second probe competes with the polynucleotide target for binding to the first probe and the first probe preferentially binds to the polynucleotide target rather than to the second probe. Upon hybridization of the first probe to the second probe of a probe pair, the fluorescent donor and the fluorescent acceptor are spaced apart from each other a distance such that they are capable of fluorescence resonance energy transfer in response to activation of the fluorescent donor by light of the predetermined wavelength or band or wavelengths. The second step is activating more than one fluorescent donor from more than one probe pair in the mixture with light of the predetermined wavelength or band of wavelengths. The next step is detecting light emitted by the more than one fluorescent donor, fluorescent acceptor, or both fluorescent donor and acceptor from more than one probe pair.

The invention further includes a kit for performing assays for detecting a polynucleotide target in a sample. The kits comprise a first oligonucleotide probe having a first fluorescent donor or acceptor and a second oligonucleotide probe having a second fluorescent donor or acceptor. The first fluorescent donor or acceptor and the second fluorescent donor or acceptor are a fluorescent donor/acceptor pair capable of fluorescence resonance energy transfer with each other in response to activation of the first or second fluorescent donor or acceptor by light of a predetermined wavelength or band of wavelengths, and upon hybridization of the first probe to the second probe, the fluorescent donor and acceptor are spaced apart from each other a distance such that they are capable of fluorescence resonance energy transfer in response to activation of the fluorescent donor by light of the predetermined wavelength.

DRAWINGS

These features, aspects and advantages of the present invention will become better understood with regard to the following description, appended claims and accompanying figures where:

Figure 3:
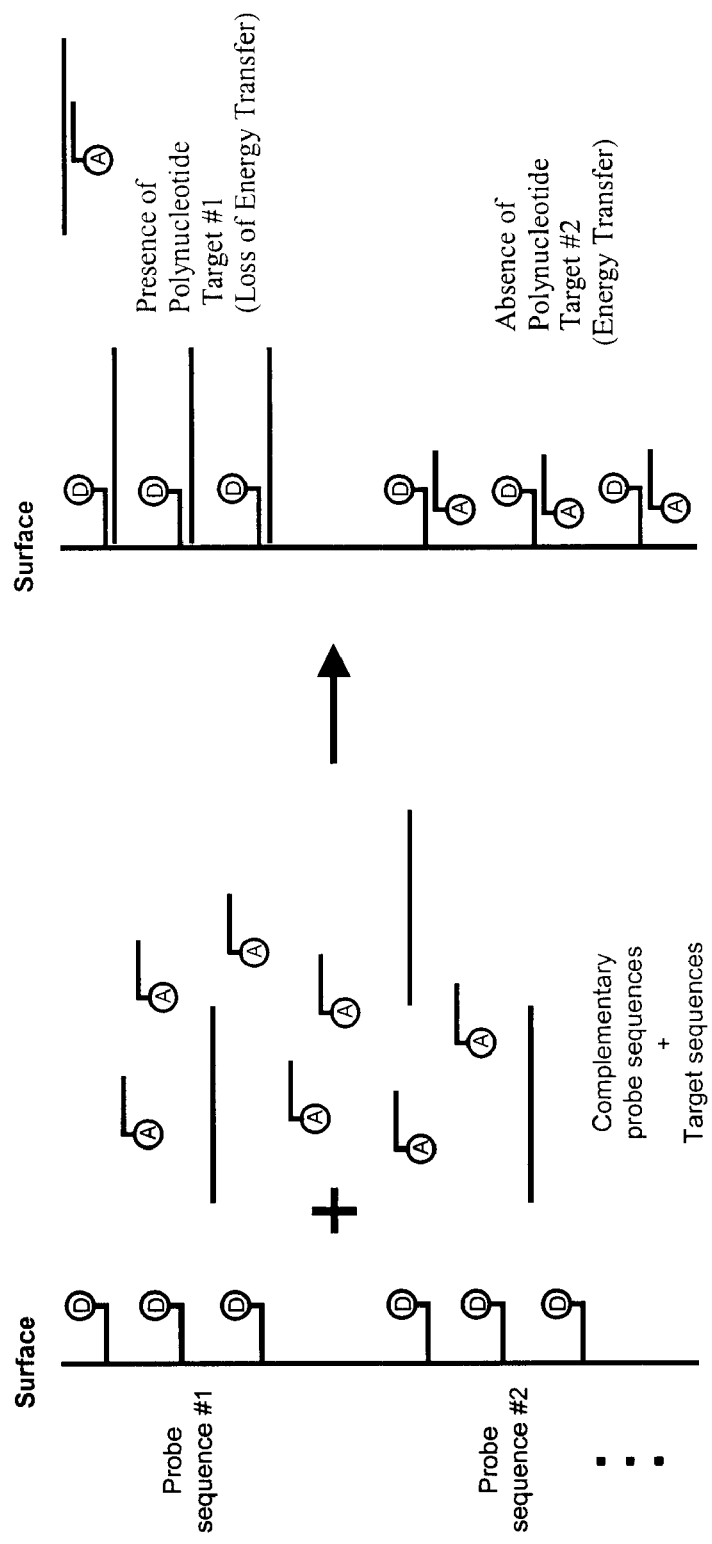
Figure 4:
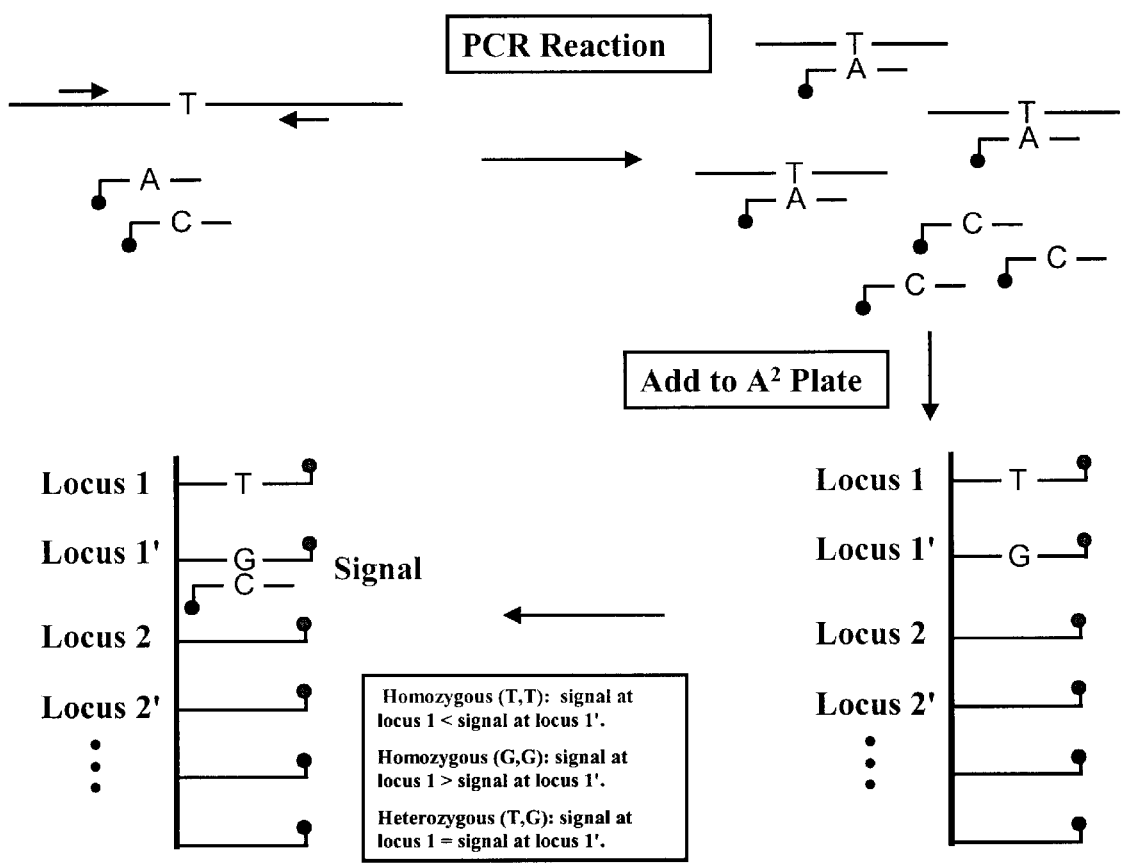

FIG. 3 illustrates a simple array scheme with two probe pairs having 3'-end labeled probes such that one probe of each pair is immobilized to a solid support; and FIG. 4 illustrates an embodiment according to the present invention where the method is used to detect multiple single nucleotide polymorphisms (SNP's) in a single reaction. Polynucleotides containing SNP's are amplified in a PCR reaction which includes a first set of probes, each first probe corresponding to a distinct probe pair. Each probe is specific for a different allele. When a particular polynucleotide target contains a given allele, the amplified product of that allele will bind to the corresponding probe. A set of second probes are immobilized onto a surface at a specific locations on the array surface. Each second probe is also specific for a single allele at an SNP locus and is able to hybridize with a corresponding first probe. Following the PCR reaction which included the first probe set, the reaction products are then allowed to hybridize to the array comprising the second probe set. Only those first set probes that had not hybridized to a target hybridize to the complementary probe and generate a signal. The first set probes are free to hybridize with the second set probes because that polynucleotide allele is not present in the sample. Parameters including probe length, salt concentration, and annealing temperature are optimized and the hybridization temperature is set below the Tm of a perfect match, but above the Tm of a single mismatch. Hybridization of such 'allele-specific oligonucleotides' is well known in the art.

DESCRIPTION

The following discussion describes embodiments of the invention and several variations of these embodiments. This discussion should not be construed, however, as limiting the invention to those particular embodiments. Practitioners skilled in the art will recognize numerous other embodiments as well. In all of the embodiments described herein that are referred to as being preferred or particularly preferred, these embodiments are not essential even though they may be preferred.

Definitions

The terms "polynucleotide" or "nucleic acid" and their respective plurals are used essentially interchangeably herein and are intended to include naturally occurring or synthesized double stranded deoxyribonucleic acid (hereinafter "DNA"), single stranded DNA, or ribonucleic acid (hereinafter "RNA").

"Perfectly Complementary" as used herein means that the polynucleotide or oligonucleotide strands making up a duplex form a double stranded structure with one another such that every nucleotide in each strand undergoes Watson-Crick base pairing with a nucleotide in the other strand and that there are no mismatches.

A "mismatch" in a duplex between a polynucleotide target and an oligonucleotide probe or primer means that a pair of nucleotides in the duplex fails to undergo Watson-Crick bonding.

An "unmatched" nucleotide in a duplex between two oligonucleotide probes is a nucleotide in a duplex or single stranded or overhanging segment of the duplex that fails to undergo Watson-Crick base pairing.

"Partially Complementary" as used herein includes polynucleotide or oligonucleotide strands containing unmatched and non-hybridizing nucleotides, but in which the remaining "matched" nucleotides undergo Watson-Crick base pairing.

The above described base pairing also comprehends the pairing of "nucleoside analogs", such as deoxyinosine, nucleosides with 2-aminopurine bases, and the like, that may be employed. As used herein, "nucleoside" includes the natural nucleosides, including 2'-deoxy and 2'-hydroxyl forms, e.g. as described in Komberg and Baker, *DNA Replication*, 2 nd Ed. (Freeman, San Francisco, 1992). "Analogs" in reference to nucleosides includes synthetic nucleosides having modified base moieties and/or modified sugar moieties that are capable of specific hybridization, e.g. described by Scheit, *Nucleotide Analogs* (John Wiley, New York, 1980); Uhlman and Peyman, *Chemical Reviews*, 90:543–584 (1990), or the like. Such analogs include synthetic nucleosides designed to enhance binding properties, reduce degeneracy, increase specificity, and the like.

The terms "hybridize" or "hybridization" are intended to include admixing of at least two nucleic acid sequences under conditions such that when at least two complementary nucleic acid sequences are present, they will form a double-stranded structure through base-pairing.

The term "oligonucleotide probe" as used herein includes linear oligomers of natural or modified monomers, a modified backbone, or modified linkages, including deoxyribonucleosides, ribonucleosides, anomeric forms thereof, peptide nucleic acids (PNAs), and the like, capable of specifically binding to a polynucleotide target by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Alternative chemistries, such as phosphorothioate, phosphoramidate, and similar such groups resulting in a non-natural backbone may also be used provided that the hybridization efficiencies of the resulting oligonucleotides is not adversely affected.

Polynucleotide Target

The invention is useful for methods of detecting the presence or absence of one or more polynucleotide targets in a one or more samples known to contain or suspected of containing the polynucleotide target. The method can also be used to quantify the amount of polynucleotide target within the sample. The method is useful for detecting unamplified polynucleotide target in a sample such as for example RNA, MRNA, rRNA, plasmid DNA, viral DNA, bacterial DNA, and chromosomal DNA. Additionally, the method of the invention is useful in conjunction with the amplification of a polynucleotide target by well known methods such as PCR, ligase chain reaction, Q-B replicase, strand-displacement amplification (SDA), rolling-circle amplification (RCA), nucleic acid sequence-based amplification (NASBA), and the like.

Oligonucleotide Probes

The oligonucleotide probes of the invention are typically 8–60 nucleotides in length, and more typically 8–35 nucleotides in length. The oligonucleotide probes were synthesized on an Applied Biosystems 394 DNA/RNA Synthesizer, using conditions recommended and reagents purchased from Beckman Coulter Inc. (Fullerton, Calif.) and from Glen Research (Sterling, Va.). The specific sequence and length of an oligonucleotide probe is partially dictated by the sequence of the polynucleotide target to which it binds. The location in which an oligonucleotide probe is complementary a polynucleotide target may be varied to achieve appropriate annealing and melting properties for a particular embodiment.

The invention is performed using one or more probe pair comprising first and second probes that are partially complementary and have at least some unmatched nucleotides. Thus, only a portion of the nucleoside bases of first probe and the second probe of a probe pair hydrogen bond and anneal under selected reaction conditions.

The degree or amount of complementarity between probes of a probe pair(s) can be expressed as a percentage in which a probe pair typically has at least 10% unmatched nucleotides (90% or less complementarity). In exemplary embodiments, the probe pairs have at least 25% unmatched nucleotides (75% or less complementarity), at least 30% unmatched nucleotides (70% or less complementarity), at least 35% unmatched nucleotides (65% or less complementarity), at least 40% unmatched nucleotides (60% or less complementarity), at least 45% unmatched nucleotides (55% or less complementarity), at least 50% unmatched nucleotides (50% or less complementarity), at least 55% unmatched nucleotides (45% or less complementarity), and at least 60% unmatched nucleotides (40% or less complementarity). In alternative exemplary embodiments the probe pairs have between 10% and 90% complementary nucleotides, between 25% and 75% complementary nucleotides, between 30% and 65% complementary nucleotides, and between 35% and 60% complementary nucleotides.

The amount of complementarity between probes of a probe pair can alternatively be expressed by the total number of complementary nucleotides. A probe pair typically has at least five complementary nucleotides between the first probe and the second probe. In exemplary embodiments, the number of complementary nucleotides between the probes of a probe pair is eight or more nucleotides, ten or more nucleotides, between five nucleotides and thirty nucleotides, between eight nucleotides and fifteen nucleotides, between ten nucleotides and fifteen nucleotides, and between ten nucleotides and thirteen nucleotides. The invention is not limited to these examples, and a greater or lessor number of complementary nucleotides between probe pairs is possible.

In the embodiment illustrated in FIG. 1A and FIG. 1B, each probe of a probe pair comprises a first segment and a second segment wherein the first segments of the probe pair are complementary and the second segments of the probe pairs are non-complementary. The method according to this embodiment is performed under conditions where the first segments of the probe pairs hybridize to each other and the second segments of the probe pair do not hybridize.

At least one oligonucleotide probe of a probe pair is complementary to a specific polynucleotide target. One probe of a probe pair hybridizes with the polynucleotide target in embodiments where the polynucleotide target is.single stranded DNA or RNA. For the sole purpose of uniformity, it will be referred to herein that the first probe of the probe pair is complementary to the polynucleotide target in such embodiments. However, it does not matter whether it is the first probe or second probe of a probe pair that is complementary to a single stranded polynucleotide target. In embodiments in which the polynucleotide target is double stranded DNA, both the first probe and second probe of the probe pair are capable of hybridizing to complementary strands of the polynucleotide target.

The degree or amount of complementarity between the probes and polynucleotide target can also be expressed as a percentage, where the first probe has a percent complementarity to the polynucleotide target and a percent complementarity to the second probe of the probe pair. The percent complementarity between the first probe and second probe is lower than the percent complementarity between the first probe and the polynucleotide target and the first probe preferentially binds to the polynucleotide target rather than to the second probe. Alternatively, the amount or degree of complementarity between the probes and polynucleotide target can be expressed as the number of complementary nucleotides. The number of complementary nucleotides between probes in a probe pair is preferably less than the number of nucleotides complementary between the first probe and the polynucleotide target.

A small amount of unmatched nucleotides between the first probe and the polynucleotide target are tolerable. Preferably, at least 90% of the nucleotides of the first probe are complementary to the polynucleotide target. More preferably, at least 95% of the nucleotides of the first probe are complementary to the polynucleotide target. In particularly preferred embodiments, the first probe is perfectly complementary to the polynucleotide target. In such embodiments, the second probe is also perfectly complementary to the polynucleotide target if the polynucleotide target is double stranded.

Labeling of Probes

The first probe comprises a first probe fluorescent donor or acceptor. The second probe comprises a second fluorescent donor or acceptor. The first fluorescent donor or acceptor and the second fluorescent donor or acceptor are selected to form a donor/acceptor pair comprising a fluorescent donor and a fluorescent acceptor capable of fluorescence resonance energy transfer with each other in response to activation the fluorescent donor by light of a predetermined wavelength or band of wavelengths.

The excitation and emission spectra of a fluorescent moiety and the moiety to which it is paired determines whether it is a fluorescent donor or a fluorescent acceptor. Examples of molecules that are used in FRET include the dye fluorescein and fluorescein derivatives such as 5-carboxyfluorescein (5-FAM), 6-carboxyfluorescein (6-FAM), fluorescein-5-isothiocyanate (FITC), 2'7'-dimethoxy-4'5'-dichloro-6-carboxyfluorescein (JOE); rhodamine and rhodamine derivatives such as N,N,N',N'-tetramethyl-6-carboxyrhodamine (TAMRA), 6-carboxyrhodamine (R6G), tetramethyl-indocarbocyanine (Cy3), tetramethyl-benzindocarbocyanine (Cy3.5), tetramethyl-indodicarbocyanine (Cy5), tetramethyl-indotricarbocyanine (Cy7), 6-carboxy-X-rhodamine (ROX); hexachloro fluorescein (HEX), tetrachloro fluorescein TET; R-Phycoerythrin, 4-(4'-dimethylaminophenylazo) benzoic acid (DABCYL), and 5-(2'-aminoethyl)aminonaphthalene-1-sulfonic acid (EDANS). Table 1 list exemplary donor and acceptor donor and acceptor pairs, including the maximum absorbance (Abs) and emission (Em) for each. The term fluorescent acceptor encompasses fluorescence quenchers. Exemplary quencher dyes are well known in the art, e.g. as described by Clegg, "Fluorescence resonance energy transfer and nucleic acids," *Methods of Enzymology*, 211:353–389 (1992), herein incorporated by reference.

TABLE I

| Donor | Abs/Em Max | Acceptor | Abs/Em Max |
|---|---|---|---|
| Fluorescein and derivatives (FITC, 5-FAM, 6-FAM, etc.) | 495/520 | Tetramethyl Rhodamine derivatives (TRITC, TAMRA, etc.) | 555/580 |

TABLE I-continued

| Donor | Abs/Em Max | Acceptor | Abs/Em Max |
|---|---|---|---|
| TET | 521/536 | TAMRA | 555/580 |
| HEX | 535/556 | TAMRA | 555/580 |
| Cy3 | 552/570 | Cy5 | 649/670 |
| Cy3 | 552/570 | Cy3.5 | 581/596 |
| Cy3.5 | 581/596 | Cy5 | 649/670 |
| R-Phycoerythrin | 546/578 | Cy5 | 649/670 |
| Cy5 | 649/670 | Cy7 | 743/767 |

Figure 1:
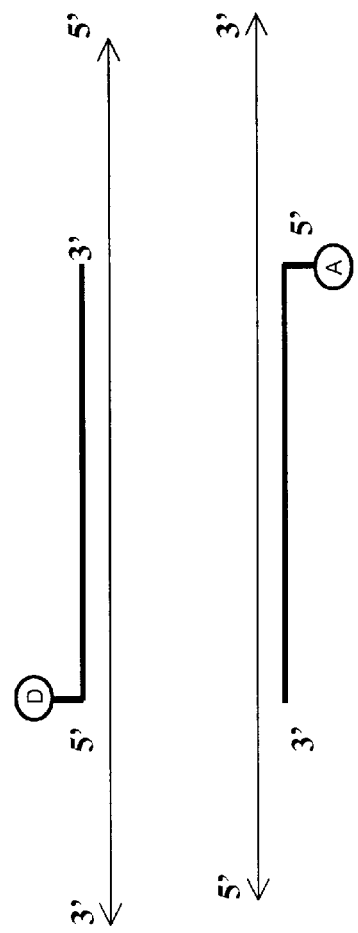
FIG. 1A illustrates a probe pair with fluorescent donor or fluorescent acceptors at the 5' ends of the oligonucleotides where the probes are hybridized to each other in the absence ot polunucleotide targer and fluorescence resonance energy transfer occurs.
FIG. 1B illustrates a probe pair with fluorescent donor or fluorescent acceptors at the 5' ends of the oligonucleotides in the presence of polynucleotide targer where there is no fluorescence resonance energy transfer.
Figure 1:
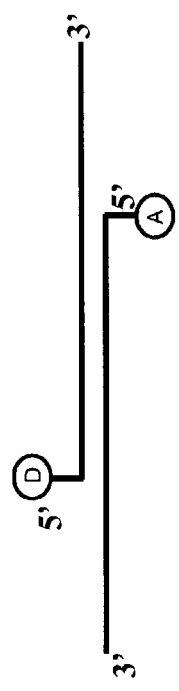
Figure 2:
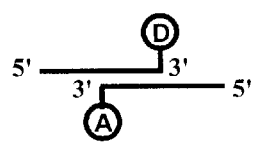
FIG. 2A illustrates a probe pair with fluorescent donor or fluorescent acceptors at the 3' ends of the oligonucleotides.
FIG. 2B illustrates this 3'-end labeled probe pair where one probe of the pair is immobilized to a solid support.
Figure 2:
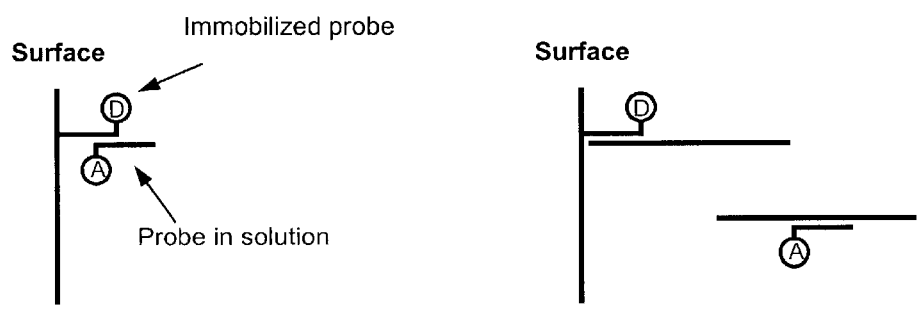

The fluorescent moieties can be incorporated or attached to the 5'-end nucleotide of an oligonucleotide probe, to the 3'-end nucleotide of an oligonucleotide probe, and to non-terminal or internal nucleotides of the oligonucleotide probes. In the embodiment of FIG. 1, fluorescent moieties are attached to the 5'-end of the first oligonucleotide probe and the 5'-end of the second oligonucleotide probe of the probe pair. In the embodiment illustrated in FIG. 2, fluorescent moieties are attached to the 3'-end of the first oligonucleotide probe and the 3'-end of the second oligonucleotide probe.

With 5'-end labeled oligonucleotides, the fluorescent moieties are typically attached to 5'-end nucleotide of the oligonucleotide probe prior to synthesis and the labeled nucleotide is incorporated into the oligonucleotide synthesis following procedures supplied by the label manufacturer (Glen Research), and as described by Yang and Millar in Methods in Enzymology, Vol. 278, pages 417–444, (1997), herein incorporated by reference.

For internal labeling, amino-modified bases are typically introduced into the oligonucleotide during synthesis using Amino-Modifier C6 dT (from Glen Research). Active-ester derivatives of the label are then coupled to the amino-modified base post-synthetically. This is advantageous because the reagents, such as cyanine-dye-labeled nucleotides, are readily available and the label does not interfere with the hybridization of the probe.

Alternative methods for attachment of fluorophores to oligonucleotides are described in Khanna et al, U.S. Pat. No. 4,351,760; Marshall; Mechnen et at, U.S. Pat. No. 5,188,934; Woo et al, U.S. Pat. No. 5,231,191; and Hobbs, Jr. U.S. Pat. No. 4,997, 928, herein incorporated by reference.

Assays and Detection

Incubating the first probe and the second probe of a probe pair under hybridizing conditions results in a hybridization complex in which the fluorescent donor and fluorescent acceptor are spaced apart from each other a distance such that they are capable of fluorescence resonance energy transfer in response to activation of the fluorescent donor by light of a predetermined wavelength. Activation and detection of the fluorescent donor and fluorescent acceptor can be performed at discrete wavelength of light or band of wavelengths such as through a filter.

The efficiency of fluorescence resonance energy transfer has been reported to be proportional to $D \times 10^{-6}$, where D is the distance between the donor and acceptor (Förster, Z. *Naturforsch A*, 1949, 4:321–327). Accordingly, fluorescence resonance energy transfer typically occurs at distances of between 10–70 Angstroms. The fluorescent donor and fluorescent acceptor are typically separated by between about 5 base-pairs (bp) and about 24 bp in a hybridized probe pair duplex. The separation distance can be less where the fluorescent acceptor is a quencher.

In preferred embodiments, the fluorescent donor and fluorescent acceptor are separated by 8 bp–18 bp in a hybridized probe pair duplex. In particularly preferred embodiments, the fluorescent donor and fluorescent acceptor are separated by 10 bp–13 bp in a hybridized probe pair duplex. As illustrated in the Figures, a probe pair hybridization complex is typically a partial duplex including unhybridized single stranded portions of each probe. Typically, the hybridization complex formed between the first probe and the second probe has a lower Tm than a hybridization complex formed between the first probe and the polynucleotide target.

Detection is performed by detecting light emitted by the fluorescent donor, the fluorescent acceptor, or both fluorescent donor and acceptor (i.e. ratio). In one embodiment, the fluorescent donor and fluorescent acceptors are both fluorophores. As illustrated in the embodiment in FIG. 1, the unhybridized probes and probes hybridizing to the polynucleotide target do not participate in fluorescence resonance energy transfer and will not produce a detectable FRET emission. The first fluorophore is activated with light of the appropriate wavelength or band of wavelengths, which is a function of the particular fluorophore. Fluorescence measurements are made using a Wallac 1420 Victor$^2$ multilabel counter, a Perkin Elmer LS50B luminescence spectrometer, or other suitable instruments. In an alternative embodiment, the fluorescent donor is a fluorophore and the fluorescent acceptor is a quencher and detection is performed by measuring the emission of the flurphore.

The invention is useful for detecting more than one polynucleotide target in one or more samples. The polynucleotide targets may reside on distinct nucleic acids, or more than one polynucleotide target may reside on a particular nucleic acid. In one embodiment, the method is performed with more than one probe pair wherein the donor/acceptor pairs of at least two probe pairs are different and the wavelength or band of wavelengths of light used for activation of the fluorescent donor of the at least two different probe pairs is distinct. In another embodiment, either the first probe or the second probe is immobilized on a solid surface. In this embodiment, in os not required that the donor/acceptor pairs of at least two probe pairs are different and the wavelength of light used for activation of the fluorescent donor of the at least two different probe pairs is distinct. The identity and specificity of each polynucleotide target is determined by the spacial localization of the probes. Alternatively, the polynucleotide targets are immobilized or attached at discrete locations to detect multiple polynucleotide targets with specificity. The detection of polynucleotide targets is useful for a variety of applications, including for example, the detection of polynucleotide targets associated with single nucleotide polymorphisms, insertions, deletions, and multiple mutations.

The invention further includes a kit for performing assays for detecting a polynucleotide target in a sample. The kit comprises a first probe labeled with a first fluorescent donor or fluorescent acceptor and a second probe labeled with a second fluorescent donor or fluorescent acceptor. The first probe is substantially complementary to the polynucleotide target, while the first and second probes are only partially complementary to each other. The first probe preferentially binds to the polynucleotide target rather than to the second probe. The second oligonucleotide probe comprises a number of nucleotides complementary to the first probe. The first probe typically comprises a number of nucleotides complementary to a select polynucleotide target that is greater than the number of nucleotides complementary to the second probe such that the first probe preferentially binds to the polynucleotide target rather than to the second probe. The first fluorescent donor or acceptor and the second fluorescent donor or acceptor are a donor/acceptor pair capable of fluorescence resonance energy transfer with each other in response to activation the fluorescent donor by light of a predetermined wavelength or band of wavelengths. When the kit is used to preform a hybridization assay, the first probe hybridizes to the second probe such that the fluorescent donor and the fluorescent acceptor are spaced apart from each other a distance such that they are capable of fluorescence resonance energy transfer in response to activation of the fluorescent donor by light of the predetermined wavelength.

EXAMPLE I

PCR Amplification of Sample

A reaction mixture was prepared by combining the following components: 4 mM MgCl$_2$; 0.4 mM dNTP's; 2.5 ng DNA template (pUC18 plasmid); 500 nM each of the primers 5'-TCATTCAGCTCCGGTTCCCAACGA-3' (SEQ ID NO:1) and 5'-GTACTCACCAGTCACAGAAAAGCA-3' (SEQ ID NO:2); 250 nM each of first and second labeled probes; 2 units recombinant Taq DNA polymerase (Cat # 10342-020; Gibco BRL); 1×PCR buffer (supplied with enzyme); up to a 50 μl total reaction volume. The samples are thermocycled for 30 cycles for 20 sec at 96° C.; 20 sec at 50° C., and 4 min at 60° C. The primers amplify a 201 bp fragment from the Amp$^r$ gene. The labeled first probe and labeled second probe do not need to be added at this stage, but are added as a matter of convenience to avoid an additional denaturation/renaturation step after PCR to allow the probes to hybridize.

EXAMPLE II

Demonstration Of Probe Function to Quantify DNA

The polynucleotide target in this example were synthesized single stranded and double stranded DNA oligonucleotide 50-mers. The double-stranded DNA target is a duplex of the following oligomers: 5'-CGGT-CCTCCGATCGTTGTCAGAAGTAAGTTGGCCGCAGT-GTTATCACTCA-3' (SEQ ID NO:3) and 5'-TGAGTGATAACACTGCGGCCAACTTACTTCTGAC-AACGATCGGAGGACCG-3' (SEQ ID NO:4), and the single stranded polynucleotide target consist of SEQ ID NO:3.

A reaction mixture was prepared by combining the following components: DNA target in different amounts ranging from 0.25 ng to 2.5 ng; 200 mM Tris, pH 8.0; 1 mM EDTA; and 50 mM NaCl; and water up to a total volume of 50 μl per sample. The DNA is denatured by heating for 3 min at 96° C. in the thermocycler, allowed to re-anneal for 5 min at 50° C., and then cooled to room temperature.

One oligonucleotide probe of the probe pair is 5'-end labeled with the fluorophore Cy3, and the other oligonucleotide probe was 5'-end labeled with the fluorophore Cy5. The labeled probes were the following: Cy3-ATCGTTGTCAGAAGTAAGTTGGCC (SEQ ID NO:5) and Cy5-TTCTGACAACGATCGGAGGACCGA (SEQ ID NO:7). There are 13 complementary bases between the two probes, which are underlined. Fluorescence measurements were made on a Wallac Victor$^2$ instrument. Cy3 emission was measured using 550 nm excitation filter with 570 nm emission filter. Cy5 emission (by energy transfer) was measured using 550 nm excitation filter with 670 nm emission filter.

As a comparison, polynucleotide target was quantified using a Molecular Beacon probe. Cy5 emission was measured using a 650 nm excitation filter with a 670 nm emission filter. All reported values represent an average of 3 relative fluorescence units (of the same sample) minus an average background signal (the emission from an empty well). The Molecular Beacon sequence is the following: Cy5-CAGAGCATCGTTGTCAGAAGTAAGTTG TGCTCTG-Dabcyl (SEQ ID NO:9). Stem sequence is underlined; target-complementary sequence is identical to first 21 bases of SEQ ID NO:4. (Molecular Beacon probe was purchased from Stratagene). For single-strand quantitation, 250 nM probe was used. For double-stranded quantitation, 2250 nM probe was used because less than 2250 nM of probe gave poor performance.

| Target DNA Concentration (nM) | Cy3 Emission[1] | Cy5 Emission | Ratio Cy3/Cy5 Emission |
|---|---|---|---|
| Probes Pair SEQ ID NO: 5/SEQ ID NO: 7; Single-Stranded DNA Target | | | |
| 0 | 41260 | 9520 | 4.3 |
| 50 | 50150 | 9195 | 5.5 |
| 100 | 68990 | 7960 | 8.7 |
| 200 | 78655 | 5900 | 13.3 |
| 300 | 84065 | 5250 | 16.0 |
| Probes Pair SEQ ID NO: 5/SEQ ID NO: 7; Double-Stranded DNA Target | | | |
| 0 | 48295 | 13370 | 3.6 |
| 50 | 51669 | 10495 | 4.9 |
| 100 | 59070 | 9830 | 6.0 |
| 200 | 64781 | 7890 | 8.2 |
| 300 | 66135 | 6235 | 10.6 |

[1]All emission data is measured in relative fluorescence units

| Target DNA Concentration (nM) | Cy5 Emission[1] |
|---|---|
| Molecular Beacon Probe; Single-Stranded DNA Target | |
| 0 | 3865 |
| 50 | 4380 |
| 100 | 5625 |
| 200 | 7115 |
| 300 | 8420 |
| Molecular Beacon Probe; Double-Stranded DNA Target | |
| 0 | 5505 |
| 50 | 4955 |
| 100 | 5483 |
| 200 | 6174 |
| 300 | 6359 |

[1]All emission data is measured in relative fluorescence units

EXAMPLE III

Comparison of Probe Pairs Having Different Degrees of Complementarity

Probes of the invention were incorporated into a PCR reaction to detect the polynucleotide amplification products. The PCR amplification was performed as described in Example I, using primers that amplify a 201 bp fragment from the Amp$^r$ gene. Probe pairs having overlapping segments of complementarity of 10, 13, and 24 nucleotides in length were used to detect the amplified fragment. The complementary regions of the probes are underlined. The first probe for each probe pair was SEQ ID NO:5 Cy3-ATCGTTGTCAGAAGTAAGTTGGCC. The second probe of the probe pair Cy5-TGACAACGAT-CGGAGGACCGAAGG having SEQ ID NO:6 has a 10-base overlap with the first probe SEQ ID NO:5. The second probe of the probe pair having SEQ ID NO:7 Cy5-TTCTGACAACGATCGGAGGACCGA has a 13-base overlap with the first probe SEQ ID NO:5. The second probe of the probe pair GGCCAACTTACTTC(Cy5-T)GACAACGAT having SEQ ID NO:8 has a 24-base overlap with the first probe SEQ ID NO:5.

Oligonucleotide probe having SEQ ID NO:6 and SEQ ID NO:7 are partially complementary to oligonucleotide having SEQ ID NO:5. SEQ ID NO:6 has a 10-base overlap with SEQ ID NO:5. SEQ ID NO:7 has a 10-base overlap with SEQ ID NO:5. SEQ.ID NO:8 is perfectly complementary to SEQ ID NO:5, and all 24 bases overlap with SEQ ID,NO:5. Fluorescence measurements from the acceptor dye were made before and after thermocycling (after 0 and 30 cycles), using 550 nm excitation and 670 nm emission filters.

| Probe Pair | 0 cycles | 30 cycles |
|---|---|---|
| SEQ ID NO: 5/SEQ ID NO: 7 (13 base-pair overlap) | 10,100 | 6,900 |
| SEQ ID NO: 5/SEQ ID NO: 6 (10 base-pair overlap) | 9,250 | 6,500 |
| SEQ ID NO: 5/SEQ ID NO: 8 (control) | 10,800 | 10,400 |
| Control reactions (leaving out Taq polymerase): | | |
| SEQ ID NO: 5/SEQ ID NO: 6 | 10,600 | 10,800 |
| SEQ ID NO: 5/SEQ ID NO: 16 | 9,400 | 10,400 |
| SEQ ID NO: 5/SEQ ID NO: 17 | 10,000 | 10,200 |

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A method for detecting a polynucleotide target in a sample, the method comprising the steps of:
   a) forming a mixture by combining:
      (i) a sample known to contain or suspected of containing the polynucleotide target;
      (ii) a first probe complementary to the polynucleotide target, the first probe comprising a first fluorescent donor or fluorescent acceptor, a first segment and a second segment;
      (iii) a second probe partially complementary to the first probe, the second probe comprising a second fluorescent donor or fluorescent acceptor, a first segment and a second segment,
         wherein the second probe competes with the polynucleotide target for binding to the first probe and the first probe preferentially binds to the polynucleotide target rather than to the second probe,
         wherein the first segments of the first and second probes are complementary and the second segments of the first and second probes are not complementary, and wherein both the first and second segments of at least the first probe are complementary to the polynucleotide target,
         wherein the first fluorescent donor or acceptor and the second fluorescent donor or acceptor are a fluorescent donor/acceptor pair capable of fluorescence resonance energy transfer with each other in response to activation of the fluorescent donor by light of a predetermined wavelength or band of wavelengths, and
         wherein upon hybridization of the first probe to the second probe the fluorescent donor and the fluorescent acceptor are spaced apart from each other a distance such that they are capable of fluorescence resonance energy transfer in response to activation of the fluorescent donor by light of the predetermined wavelength;
   b) activating the fluorescent donor in the mixture with light of the predetermined wavelength or band of wavelengths; and
   c) detecting light emitted by the fluorescent donor, the fluorescent acceptor, or both fluorescent donor and acceptor.

2. The method of claim 1 wherein the first and second probes are oligonucleotides and the first probe has a greater number of nucleotides that are complementary to the polynucleotide target than to the second probe.

3. The method of claim 1, wherein the first and second segments of the first probe and the first and second segments of the second probe are complementary to the polynucleotide target.

4. The method of claim 1 wherein the amount of polynucleotide target detected is inversely related to the amount of fluorescence resonance energy transfer between the first fluorescent donor or fluorescent acceptor and the second fluorescent donor or fluorescent acceptor.

5. The method of claim 1 wherein the first and second probes are oligonucleotides, and wherein the first probe, the second probe, or both probes comprise at least five nucleotides that are complementary to the polynucleotide target.

6. The method of claim 1 wherein the first probe is perfectly complementary to the polynucleotide target.

7. The method of claim 1 wherein the first probe and the second probe have between 10% and 90% complementary nucleotides.

8. The method of claim 1, wherein the first probe and the second probe have between 25% and 75% complementary nucleotides.

9. The method of claim 1, wherein the first probe and the second probe have between five and thirty complementary nucleotides.

10. The method of claim 1 wherein the first fluorescent donor or acceptor and the second fluorescent donor or acceptor are attached to the 5' end of the probes.

11. The method of claim 1 wherein the first fluorescent donor or acceptor and the second fluorescent donor or acceptor are attached to the 3' end of the probes.

12. The method of claim 1 wherein the first and second probes are oligonucleotides and the fluorescent donor and the fluorescent acceptor are separated by between 8 bp and 18 bp upon hybridization of the first and second probe.

13. The method of claim 1 wherein the first and second probes are oligonucleotides and the fluorescent donor and the fluorescent acceptor are separated by between 10 bp and 13 bp upon hybridization of the first and second probe.

14. The method of claim 1 wherein the step of forming the reaction mixture is performed with a polynucleotide target that is an amplification product.

15. The method of claim 1 wherein the polynucdeotide target is amplified and real time detection of the amplified sample is performed.

16. The method of claim 1 further comprising the step of quantifying the amount of polynucleotide target in the sample.

17. The method of claim 1 wherein the method is performed to detect single nucleotide polymorphisms, insertions, deletions, and multiple mutations.

18. The method of claim 1 wherein either the first probe or the second probe is immobilized on a solid surface.

19. The method of claim 1 wherein the polynucleotide target is double stranded and the second probe is complementary to at least a portion of the polynucleotide target.

20. The method of claim 1 wherein one or more probes comprises an oligonucleotide having a modified backbone.

21. The method of claim 1 wherein the polynucleotide target is single stranded and the second probe is not complementary to the polynucleotide target.

22. The method of claim 21, wherein the polynucleotide target is RNA.

23. A method for detecting more than one polynucleotide target in a sample, the method comprising the steps of:

a) forming a mixture by combining:
  (i) one or more samples known to contain or suspected of containing more than one polynucleotide target;
  (ii) more than one probe pair, each probe pair comprising a first probe and a second probe, each probe of a probe pair comprising a fluorescent donor or acceptor, a first segment and a second segment, wherein each probe pair comprises a fluorescent donor/acceptor pair capable of fluorescence resonance energy transfer in response to activation of the fluorescent donor by light of a predetermined wavelength or band of wavelengths,
    wherein for each probe pair the first probe is complementary to the polynucleotide target and the second probe of a probe pair is partially complementary to the first probe, and wherein the second probe competes with the polynucleotide target for binding to the first probe and the first probe preferentially binds to the polynucleotide target rather than to the second probe,
    wherein the first segments of the first and second probes are complementary and the second segments of the first and second probes are not complementary, and wherein both the first and second segments of at least the first probe are complementary to the polynucleotide target; and
    wherein upon hybridization of the first probe to the second probe of a probe pair the fluorescent donor and the fluorescent acceptor are spaced apart from each other a distance such that they are capable of fluorescence resonance energy transfer in response to activation of the fluorescent donor by light of the predetermined wavelength or band or wavelengths;
b) activating more than one fluorescent donor from more than one probe pair in the mixture with light of the predetermined wavelength or band or wavelengths; and
c) detecting light emitted the more than one fluorescent donor, fluorescent acceptor, or both fluorescent donor and acceptor from more than one probe pair.

24. The method of claim 23, wherein the more than one polynucleotide targets are immobilized to a solid support at different positions.

25. The method of claim 23, wherein one probe of each probe pair is immobilized to a solid support.

26. The method of claim 23, wherein the donor/acceptor pairs of at least two probe pairs are different and the wavelength of light used for activation of the fluorescent donor of the at least two different probe pairs is distinct.

27. The method of claim 23, wherein each probe pair detects single nucleotide polymorphisms, insertions, deletions, or multiple mutations.

28. The method of claim 27, wherein one probe of each probe pair is immobilized to a solid support.

29. A kit for detecting a polynucleotide target in a sample, comprising:

a) a first probe complementary to the polynucleotide target, the first probe comprising a first fluorescent donor or fluorescent acceptor, a first segment, and a second segment;
b) a second probe partially complementary to the first probe, the second probe comprising a second fluorescent donor or fluorescent acceptor, a first segment and a second segment; and
  wherein the second probe competes with the polynucleotide target for binding to the first probe and the first probe preferentially binds to the polynucleotide target rather than to the second probe, wherein the first segments of the first and second probes are complementary and the second segments of the first and second probes are not complementary, and wherein both the first and second segments of at least the first probe are complementary to the polynucleotide target, wherein the first fluorescent donor or acceptor and the second fluorescent donor or acceptor are a fluorescent donor/acceptor pair capable of fluorescence resonance energy transfer with each other in response to activation of the fluorescent donor by light of a predetermined wavelength or band of wavelengths, and wherein upon hybridization of the first probe to the second probe the fluorescent donor and the fluorescent acceptor are spaced apart from each other a distance such that they are capable of fluorescence resonance energy transfer in response to activation of the fluorescent donor by light of the predetermined wavelength or band of wavelengths.

* * * * *

SEQUENCE LISTING

<160> NUMBER OF SEQ ID NOS: 9

<210> SEQ ID NO 1
<211> LENGTH: 24
<212> TYPE: DNA
<213> ORGANISM: Escherichia coli

<400> SEQUENCE: 1
tcattcagct ccggttccca acga                                               24

<210> SEQ ID NO 2
<211> LENGTH: 24
<212> TYPE: DNA
<213> ORGANISM: Escherichia coli

<400> SEQUENCE: 2
gtactcacca gtcacagaaa agca                                               24

<210> SEQ ID NO 3
<211> LENGTH: 50
<212> TYPE: DNA
<213> ORGANISM: Escherichia coli

<400> SEQUENCE: 3
cggtcctccg atcgttgtca gaagtaagtt ggccgcagtg ttatcactca                   50

<210> SEQ ID NO 4
<211> LENGTH: 50
<212> TYPE: DNA
<213> ORGANISM: Escherichia coli

<400> SEQUENCE: 4
tgagtgataa cactgcggcc aacttacttc tgacaacgat cggaggaccg                   50

<210> SEQ ID NO 5
<211> LENGTH: 24
<212> TYPE: DNA
<213> ORGANISM: Escherichia coli
<220> FEATURE:
<221> NAME/KEY: modified_base
<222> LOCATION: (1)..(1)
<223> OTHER INFORMATION: Labeled with fluorophore dye tetramethyl-
      indodicarbocyanine
<221> NAME/KEY: modified_base
<222> LOCATION: (1)..(1)
<223> OTHER INFORMATION: Labeled with fluorophore dye tetramethyl-
      indocarbocyanine

<400> SEQUENCE: 5
atcgttgtca gaagtaagtt ggcc                                               24

<210> SEQ ID NO 6
<211> LENGTH: 24
<212> TYPE: DNA
<213> ORGANISM: Escherichia coli
<220> FEATURE:
<221> NAME/KEY: modified_base
<222> LOCATION: (1)..(1)
<223> OTHER INFORMATION: Labeled with fluorophore dye tetramethyl-
      indodicarbocyanine

<400> SEQUENCE: 6
tgacaacgat cggaggaccg aagg                                               24

```
<210> SEQ ID NO 7
<211> LENGTH: 24
<212> TYPE: DNA
<213> ORGANISM: Escherichia coli
<220> FEATURE:
<221> NAME/KEY: modified_base
<222> LOCATION: (1)..(1)
<223> OTHER INFORMATION: Labeled with fluorophore dye tetramethyl-
      indodicarbocyanine

<400> SEQUENCE: 7
ttctgacaac gatcggagga ccga                                              24

<210> SEQ ID NO 8
<211> LENGTH: 23
<212> TYPE: DNA
<213> ORGANISM: Escherichia coli
<220> FEATURE:
<221> NAME/KEY: modified_base
<222> LOCATION: (15)..(15)
<223> OTHER INFORMATION:
<221> NAME/KEY: modified_base
<222> LOCATION: (15)..(15)
<223> OTHER INFORMATION: Labeled with fluorophore dye tetramethyl-
      indodicarbocyanine

<400> SEQUENCE: 8
ggccaactta cttcgacaac gat                                               23

<210> SEQ ID NO 9
<211> LENGTH: 34
<212> TYPE: DNA
<213> ORGANISM: Escherichia coli
<220> FEATURE:
<221> NAME/KEY: modified_base
<222> LOCATION: (1)..(1)
<223> OTHER INFORMATION: Labeled with fluorophore dye tetramethyl-
      indodicarbocyanine
<221> NAME/KEY: modified_base
<222> LOCATION: (34)..(34)
<223> OTHER INFORMATION: Labeled with fluorophore dye R-Phycoerythrin,
      4-(4'-dimethylamino phenylazo) benzoic acid

<400> SEQUENCE: 9
cagagcatcg ttgtcagaag taagttgtgc tctg                                   34
```